(12) United States Patent
Euliano, II et al.

(10) Patent No.: US 7,828,753 B2
(45) Date of Patent: Nov. 9, 2010

(54) ELECTRODE INTERFACE SYSTEM

(75) Inventors: Neil Russell Euliano, II, Gainesville, FL (US); Dorothee Marossero, Gainesville, FL (US)

(73) Assignee: Convergent Engineering, Inc., Gainesville, FL (US)

( * ) Notice: Subject to any disclaimer, the term of this patent is extended or adjusted under 35 U.S.C. 154(b) by 0 days.

(21) Appl. No.: 11/582,714

(22) Filed: Oct. 18, 2006

(65) Prior Publication Data

US 2008/0139967 A1  Jun. 12, 2008

(51) Int. Cl.
*A61B 5/00* (2006.01)
*A61B 5/04* (2006.01)
*A61B 5/0488* (2006.01)
*A61B 5/103* (2006.01)
*H01R 11/00* (2006.01)

(52) U.S. Cl. .................. 600/588; 600/304; 600/376; 439/502

(58) Field of Classification Search .................. 600/588, 600/304, 376; 439/502
See application file for complete search history.

(56) References Cited

U.S. PATENT DOCUMENTS

| | | | | |
|---|---|---|---|---|
| 4,781,200 A | * | 11/1988 | Baker | ............... 600/588 |
| 4,967,761 A | | 11/1990 | Nathanielsz | |
| 4,987,898 A | * | 1/1991 | Sones | ............... 600/398 |
| 5,301,680 A | * | 4/1994 | Rosenberg | ............... 600/588 |
| 5,373,852 A | | 12/1994 | Harrison et al. | |
| 5,442,940 A | * | 8/1995 | Secker et al. | ............... 600/588 |
| 5,483,970 A | | 1/1996 | Rosenberg | |
| 5,546,953 A | | 8/1996 | Garfield | |
| 5,623,939 A | | 4/1997 | Garfield | |
| 5,671,749 A | * | 9/1997 | Hon | ............... 600/588 |
| 5,776,073 A | | 7/1998 | Garfield et al. | |
| 6,421,558 B1 | * | 7/2002 | Huey et al. | ............... 600/546 |
| 6,663,570 B2 | * | 12/2003 | Mott et al. | ............... 439/909 |
| 6,694,192 B2 | | 2/2004 | Policker et al. | |
| 6,816,744 B2 | | 11/2004 | Garfield et al. | |
| 6,823,211 B2 | | 11/2004 | Simpson et al. | |
| 6,879,858 B1 | | 4/2005 | Adams | |

(Continued)

FOREIGN PATENT DOCUMENTS

WO    WO 86/02250    4/1986

(Continued)

OTHER PUBLICATIONS

Garfield et al., "Comparing uterine electromyography activity of antepartum patients versus term labor patients," *American Journal of Obstetrics and Gynecology*, Jul. 2005, pp. 23-29, vol. 193, No. 1.

(Continued)

*Primary Examiner*—Max Hindenburg
*Assistant Examiner*—Emily M Lloyd
(74) *Attorney, Agent, or Firm*—Saliwanchik, Lloyd & Saliwanchik

(57) ABSTRACT

An electrode interface system for providing a connection between at least one electrode and a maternal-fetal monitor, wherein the interface system converts electrical muscle activity captured by the electrode(s) into uterine activity data signals for use by the maternal-fetal monitor. The electrode interface system of the invention preferably includes a conversion means for converting the signals from the electrode(s) into signals similar to those produced by a tocodynometer.

16 Claims, 12 Drawing Sheets

U.S. PATENT DOCUMENTS

| | | | |
|---|---|---|---|
| 6,898,460 | B2 | 5/2005 | Hoctor et al. |
| 2002/0010494 | A1 | 1/2002 | Policker et al. |
| 2002/0193670 | A1* | 12/2002 | Garfield et al. ............ 600/546 |
| 2002/0193701 | A1 | 12/2002 | Simpson et al. |
| 2003/0135130 | A1 | 7/2003 | Hoctor et al. |
| 2005/0105644 | A1 | 5/2005 | Baxter et al. |
| 2005/0267376 | A1 | 12/2005 | Marossero |
| 2006/0149168 | A1 | 7/2006 | Czarnek |
| 2007/0260133 | A1* | 11/2007 | Meyer ........................ 600/393 |
| 2008/0082024 | A1* | 4/2008 | Meyer et al. ................ 600/588 |

FOREIGN PATENT DOCUMENTS

| | | |
|---|---|---|
| WO | WO 03/028550 | 4/2003 |
| WO | WO 2004/084087 | 9/2004 |
| WO | WO 2005/052848 | 6/2005 |

OTHER PUBLICATIONS

Garfield et al., "Use of uterine EMG and cervical LIF in monitoring pregnant patients," *BJOG: An International Journal of Obstetrics and Gynecology*, Mar. 2005, pp. 103-108, vol. 112, Suppl. 1.

Garfield et al., "Uterine Electromyography and Light-Induced Fluorescence in the Management of Term and Preterm Labor," *J Soc Gynecol Investig*, Sep.-Oct. 2002, pp. 265-275, vol. 9, No. 5.

Khalil et al., "Uterine EMG Analysis: A Dynamic Approach for Change Detection and Classification," *IEEE Transactions on Biomedical Engineering*, Jun. 2000, pp. 748-756, vol. 47, No. 6.

Leman et al., "Use of the Electrohysterogram Signal Characterization of Contractions During Pregnancy," *IEEE Transactions on Biomedical Engineering*, Oct. 1999, pp. 1222-1229, vol. 46, No. 10.

Marque et al., "Uterine EHG Processing for Obstetrical Monitoring," *IEEE Transactions on Biomedical Engineering*, Dec. 1986, pp. 1182-1186, vol. BME-33, No. 12.

Shafik, "Electrohysterogram: Study of the electromechanical activity of the uterus in humans," *European Journal of Obstetrics & Gynecology and Reproductive Biology*, May 1997, pp. 85-89, vol. 73, No. 1.

Verdenik et al., "Uterine electrical activity as predictor of preterm birth in women with preterm contractions," *European Journal of Obstetetrics & Gynecology and Reproductive Biology*, Apr. 2001, pp. 149-153, vol. 95, No. 2.

\* cited by examiner

ELECTRODE INTERFACE SYSTEM

BACKGROUND OF INVENTION

Assessment of the fetus during pregnancy, and particularly during labor and delivery, is an essential yet elusive goal. While most patients will deliver a healthy child with or without monitoring, more than 5 out of every 1,000 deliveries of a viable fetus near term are stillborn, with half having an undetermined cause of death. (National Vital Statistics System (NVSS), CDC, NCHS as published in "Healthy People 2010, Understanding and Improving Health: Chapter 16," co-authored by the Centers for Disease Control and Prevention and Health Resources and Services Administration, $2^{nd}$ Edition, U.S. Government Printing Office, November 2000). The risk of this unfortunate consequence is increased in a subgroup of "high risk" patients (e.g., diabetics). In addition to regular obstetric observation, after 23 weeks gestation antepartum ("in utero") fetal monitoring consists of the following (in order of complexity):

1. maternal report of fetal movement;
2. non-stress test (NST)—monitor fetal heart rate (FHR) by ultrasound, looking for baseline rate, variability and presence of accelerations above the baseline;
3. contraction stress test (CST)—response of the FHR to uterine contractions, either natural or induced; and
4. biophysical profile (BPP)—NST plus ultrasonographic evaluation of fetal movements and amniotic fluid volume.

Despite their wide acceptance, these tests offer limited predictive value, and give only a glimpse of the fetus at the time of testing. For high risk patients, once or twice weekly surveillance is often indicated, entailing both expense and inconvenience for the patient.

Intrapartum fetal surveillance is accomplished routinely with intermittent auscultation or continuous Doppler monitoring of the FHR, together with palpation or tocodynamometry (strain gauge) monitoring of contractions. When indicated, more invasive monitors are available, but require ruptured membranes/adequate cervical dilation, and entail some risk, primarily infectious. These monitors include, without limitation:

1. fetal scalp electrode—a wire electrode inserted into the fetal scalp;
2. intra-uterine pressure catheter (IUPC)—enables quantitative measurement of contractions; and
3. fetal scalp sampling—a blood sample drawn for pH analysis.

Contraction detection allows monitoring of the progress of labor. A device commonly used in monitoring contractions is the tocodynamometer. The tocodynamometer detects physical changes in the curvature of the mother's abdomen (usually with a strap or belt that is placed about the abdomen) during a contraction and translates these changes into a printed curve. The tocodynamometer detects only the presence or absence of tension on the abdomen (whether from uterine contraction or maternal movement), and often fails in the presence of obesity. Unfortunately, patients are recommended to remain in a supine position when using a tocodynamometer to monitor labor, which has been found to be the least effective physiological position for encouraging fetal internal rotation and often causes maternal hypotension and discomfort.

When cervical dilation lags behind the anticipated labor curve, oxytocin is often indicated to induce a more effective contraction pattern. Safe titration of the oxytocin may require accurate determination of "Montevideo units" which measure the strength of uterine contractions over 10 minutes. This requires the more invasive IUPC, a catheter placed into the uterus, alongside the fetus, to measure the pressure generated by uterine contractions.

The rationale for use of intrapartum electronic fetal monitoring (EFM) assumes that FHR abnormalities accurately reflect hypoxia (inadequate oxygen to the fetus), and that early recognition of this could induce intervention to improve outcome for both mother and fetus. Unfortunately, numerous studies have failed to identify this improved outcome with the use of EFM in low-risk deliveries. In fact some studies have actually shown an increase in morbidity from a higher operative delivery rate. Perhaps this should not be surprising in light of the variability in interpretation of FHR tracings and their lack of specificity for hypoxia. Yet, continuous EFM remains the standard of care in US hospitals, in large part due to medical and legal concerns.

Uterine contractions are the result of the coordinated actions of individual myometrial cells. At the cellular level, the contractions are triggered by a voltage signal called an action potential. During pregnancy, cellular electrical connectivity increases such that the action potential propagates to produce a coordinated contraction involving the entire uterus. The action potential during a uterine contraction can be measured with electrodes placed on the maternal abdomen resulting in a uterine EMG signal (hereinafter referred to as "EHG": electrohysterogram). Specifically, the EHG signal can be processed to produce a signal that is similar to the standard uterine activity signal from the tocodynamometer or IUPC. The EHG provides contraction frequency and duration information. To date, EHG signals have not been used in assessing the intra-uterine pressure or predicting montevideo units.

Postpartum, continuous uterine contraction is required to minimize uterine bleeding from the placental detachment site. Hemorrhage is the leading cause of peripartum maternal death, and most of these are postpartum hemorrhage due to this "uterine atony." Current monitoring consists of serial uterine palpation at intervals of several hours. Diagnosis is usually made by patient complaint of severe bleeding, or hypovolemic shock (from hemorrhage). Neither IUPC nor tocodynamometer monitoring is available at this time. The EHG would provide a unique means for monitoring the uterine tone, providing an early warning of atony and potential hemorrhage.

Devices that utilize invasive techniques for monitoring fetal health include those disclosed in U.S. Pat. Nos. 6,594,515; 6,115,624; 6,058,321; 5,746,212; 5,184,619; 4,951,680; and 4,437,467.

Accordingly, a cost-effective, more reliable system and method for non-invasively measuring uterine activity, in particular contractions during labor, without the need for expensive equipment replacement would be beneficial.

BRIEF SUMMARY OF THE INVENTION

The present invention provides a unique interface system that converts electrical muscle activity captured by common electrodes (such as for ECG/EMG) into signals that provide uterine activity data to a maternal-fetal monitor without the use of a tocodynamometer. Preferably, the interface system comprises a cable that converts output from electrodes to an output comparable to those provided by a tocodynamometer for connection to a maternal-fetal monitor configured for a uterine activity sensor (such as a tocodynamometer, an intrauterine pressure catheter, a fetal scalp electrode, and the like).

In one embodiment, the interface system of the invention comprises an interface (also referred to herein as a connector) for at least one electrode, an interface for a compatible port in a maternal-fetal monitor, and a signal converter for converting electrode output provided through the electrode interface to output comparable to those provided by a tocodynamometer.

In one embodiment, the interface system comprises a cable portion formed integrally with an electrode interface, a maternal-fetal monitor port interface, and a signal converter to provide a unitary cable structure. In another embodiment, the interface system comprises an electrode interface that includes a wireless signal transmitter, a maternal-fetal monitor port interface, and a signal converter that includes a wireless signal receiver, wherein all of these components are physically independent from each other.

In a preferred embodiment, the interface system comprises an electrode interface for multiple electrodes, more preferably between 2 and 6 electrodes. Preferably, the maternal-fetal monitor port interface is operably connectable with a uterine activity port or a tocodynamometer port available on the maternal-fetal monitor.

The present invention provides a new and improved interface system that has the ability to provide accurate contraction data by converting electrode signals into tocodynamometer-comparable data that can be processed using commercially available maternal-fetal monitors. The present invention is particularly advantageous because of low costs of manufacture with regard to both materials and labor, which accordingly induces low prices of sales to the consuming public.

Other features and advantages of the invention will be apparent from the following description and accompanying drawings.

DETAILED DISCLOSURE

The present invention provides a unique interface system that converts electrical muscle activity signals captured by at least one electrode into signals that provide uterine activity data to a conventional maternal-fetal monitor without the use of a tocodynamometer or invasive maternal-fetal monitoring device (such as an intra-uterine pressure catheter (IUPC) or fetal scalp electrode). The information provided by the interface system can then be processed by the maternal-fetal monitor to generate information regarding EHG signals, uterine contraction during and after labor, uterine atony, intrauterine pressure, Montevideo units, and the like.

Figure 1:
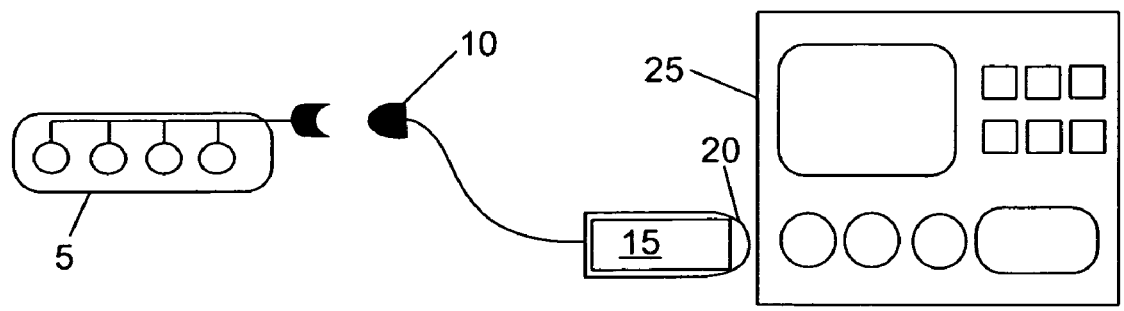
FIG. 1 illustrates one embodiment of the invention wherein an interface cable of the invention is operatively connected to a strip of electrodes and a maternal-fetal monitor.

In one embodiment, as illustrated in FIG. 1, the interface system comprises a cable integrally formed with an electrode interface 10 (or also referred to herein as a connector), a maternal-fetal monitor port interface 20, and a signal converter 15 that converts output signals from electrodes to an output signal comparable to those provided by a tocodynamometer or IUPC. The interface system is preferably in the form of a unitary cable structure. The electrode interface 10 can be connected to any conventional electrode or set of electrodes 5.

The cable can transmit analog, digital, or a combination of analog and digital signals. In certain embodiments, the cable is specifically designed for communication/connection with a conventional maternal-fetal monitor 25. For example, a cable can be preprogrammed with the expected voltage range for the monitor.

Figure 2:
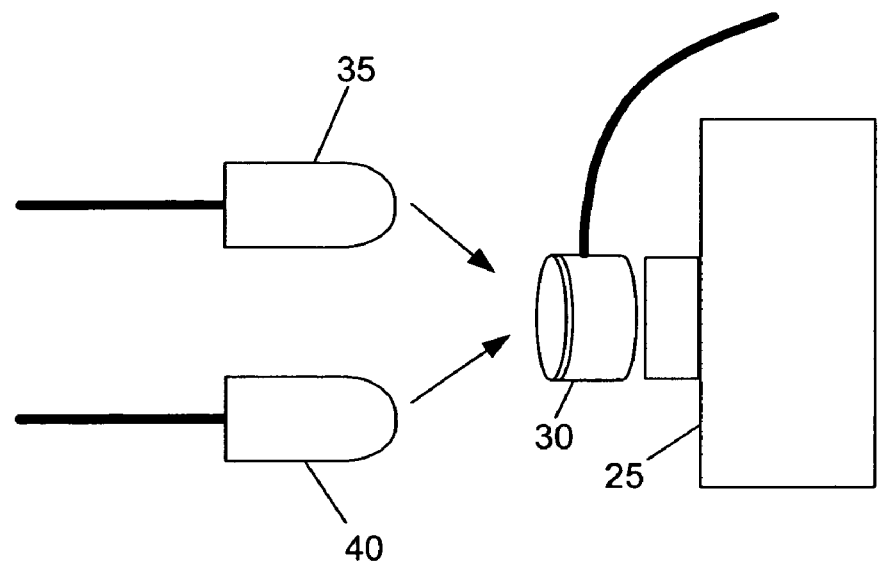
FIG. 2 illustrates a power adapter that can be used in combination with the interface cable of the invention.

In a related embodiment, the cable uses the same power as that supplied by the maternal-fetal monitor, and thus will not require a separate power supply. In certain embodiments, as illustrated in FIG. 2, an additional power connector is included in the system that allows for permanent power connectivity. The power connector can be designed as a semi-permanent adapter 30 connected to the maternal-fetal monitor that allows both standard tocodynamometer (or IUPC) cables 35 and an EHG cable 40 to be plugged into it without removing the adapter from the monitor 25. In this way, the power system can be attached to the monitor once and not removed, allowing repeated swapping of the tocodynamometer (or IUPC) cable and the interface system of the present invention without undue hassle.

The electrode interface can be connected to any conventional electrode or set of electrodes including, but not limited to, disposable electrodes (including electrodes that are without gel and pregelled), reusable disc electrodes (including gold, silver, stainless steel, or tin electrodes), headbands, and saline-based electrodes. Contemplated electrodes include those used for monitoring electrocardiography (ECG/EKG); electroencephalography (EEG); electromyography (EMG); electonystagmography (ENG); electro-oculography (EOG), printed circuit electrodes, and electroretinography (ERG).

Figure 3:
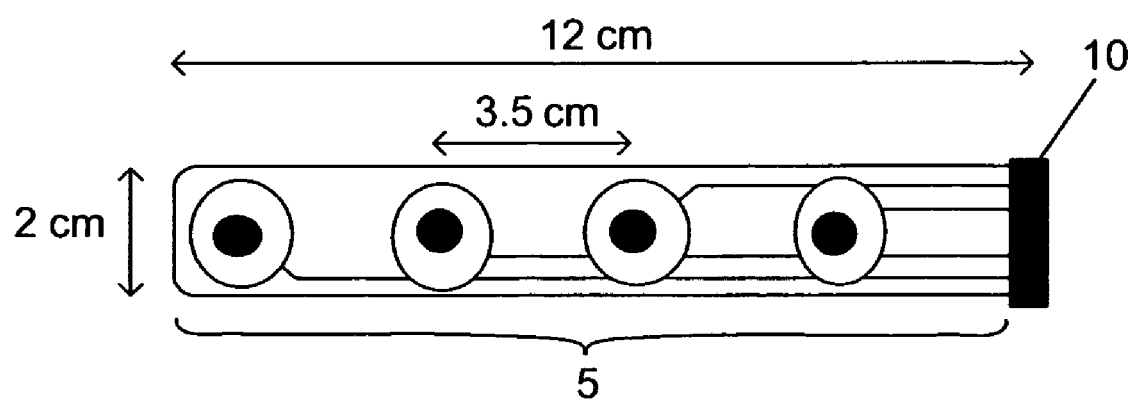
FIG. 3 illustrates a strip of electrodes that can be used in combination with the interface cable of the invention.

In a preferred embodiment, as illustrated in FIG. 3, the interface system comprises an electrode interface for a plurality of electrodes, more preferably between 2 and 6 electrodes. Preferably, the electrodes 5 are provided on a strip or mesh, including a single connector for the electrode interface 10 of the invention. The electrodes can be bipolor or monopolar in nature. The electrodes are preferably Ag/AgCl sensors with a surface area of 27 $mm^2$ wet gel. In certain related embodiments, there is an adhesive area surrounding the sensor area. The electrodes can be placed in a wide variety of locations on the patient, including over the uterus.

Figure 6:
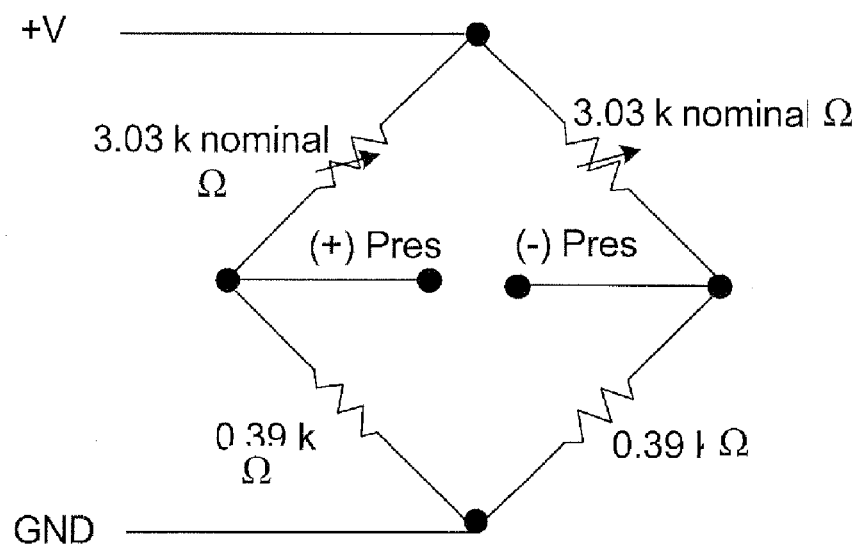
FIG. 6 illustrates one process for producing an electrical analog equivalent to a tocodynamometer signal from electrode signals.
Figure 7:
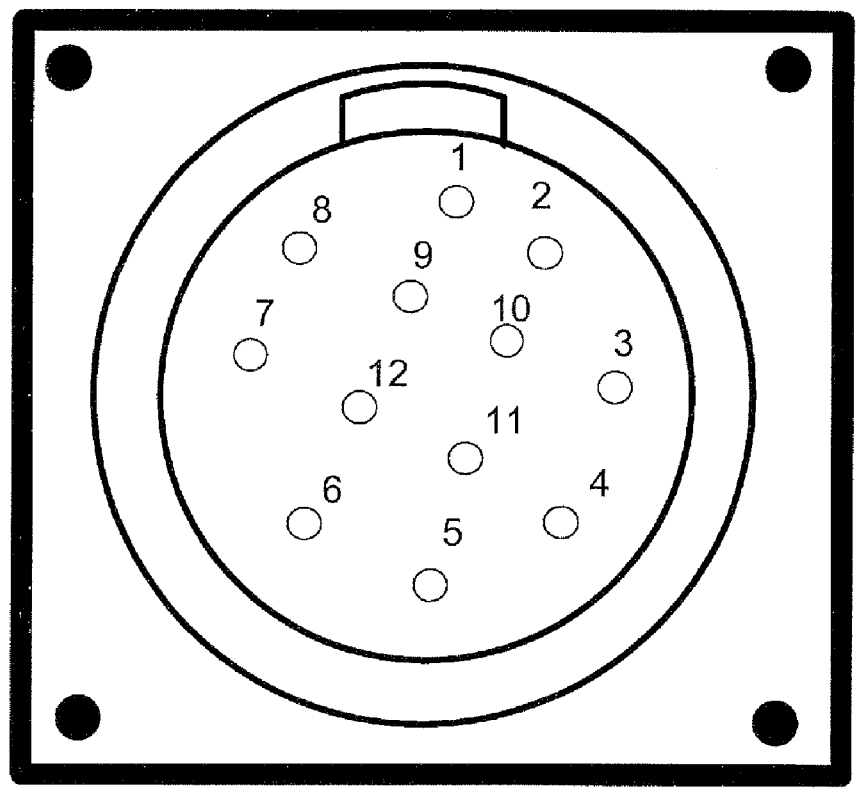
FIG. 7 illustrates a uterine activity connector pinout in a maternal-fetal monitor.
Figure 8A:
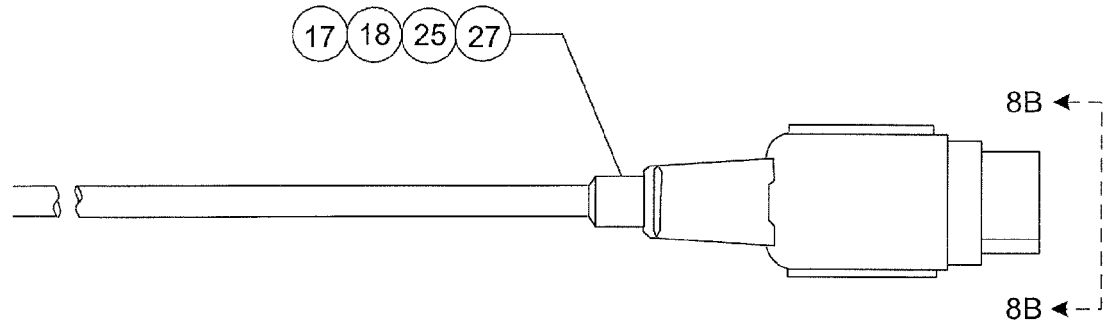
FIGS. 8A-8C illustrate a square-type cable for interfacing a fetal scalp electrode with a maternal-fetal monitor, including the cable pinout diagram and a "square-type" connector pinout for the fetal scalp electrode cable in a maternal-fetal monitor.
Figure 8B:
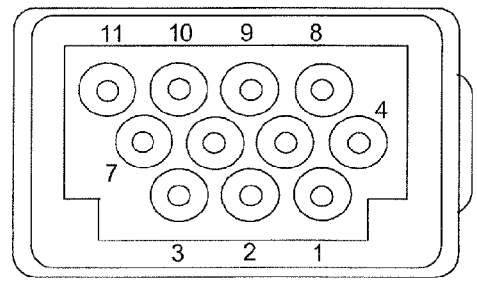
Figure 8C:
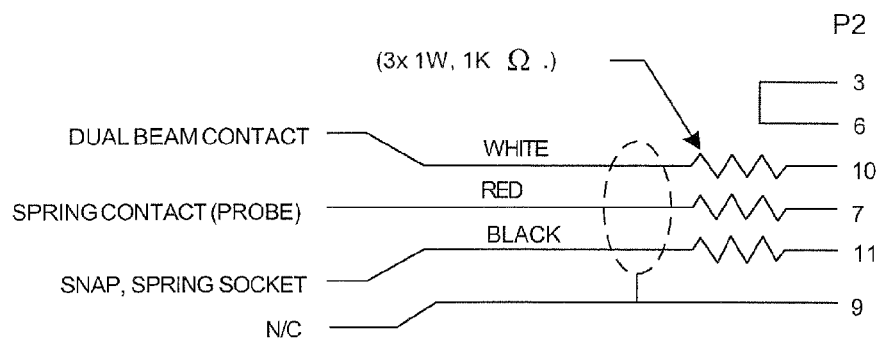
Figure 9A:
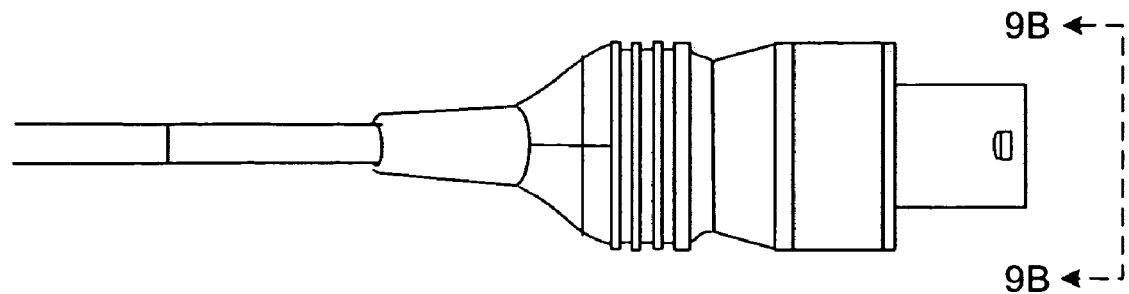
FIGS. 9A-9C illustrate another cable for interfacing a fetal scalp electrode with a maternal-fetal monitor, including the cable pinout diagram and a "circular-type" connector pinout for the fetal scalp electrode cable in a maternal-fetal monitor.
Figure 9B:
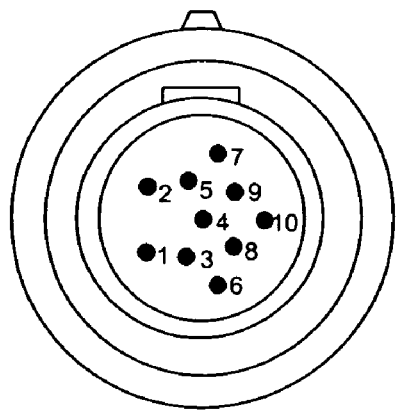
Figure 9C:
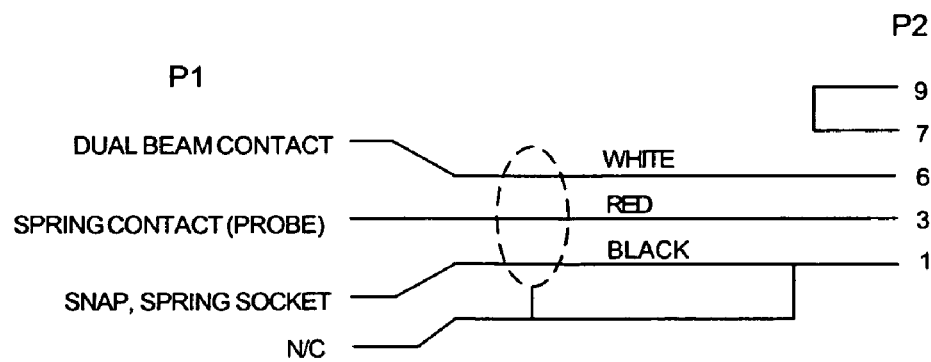
Figure 10A:
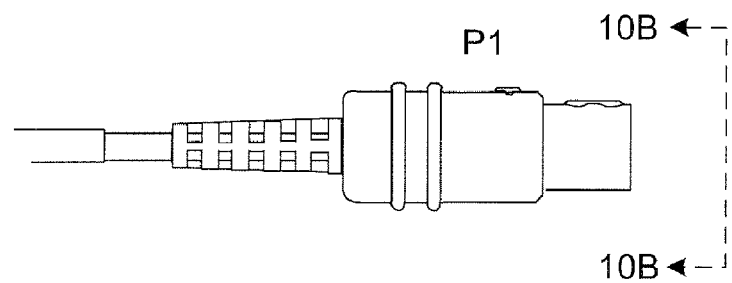
FIGS. 10A-10C illustrate a cable for interfacing an intra-uterine pressure catheter (IUPC) with a maternal-fetal monitor, including the cable pinout diagram and a "circular-type" connector pinout for the IUPC cable in a maternal-fetal monitor.
Figure 10B:
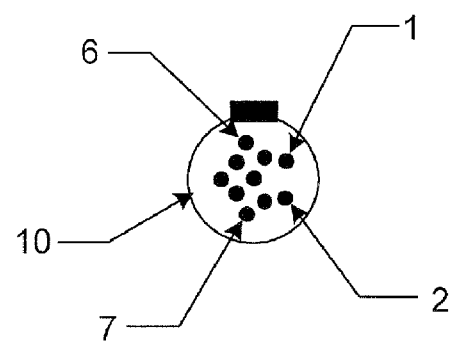
Figure 10C:
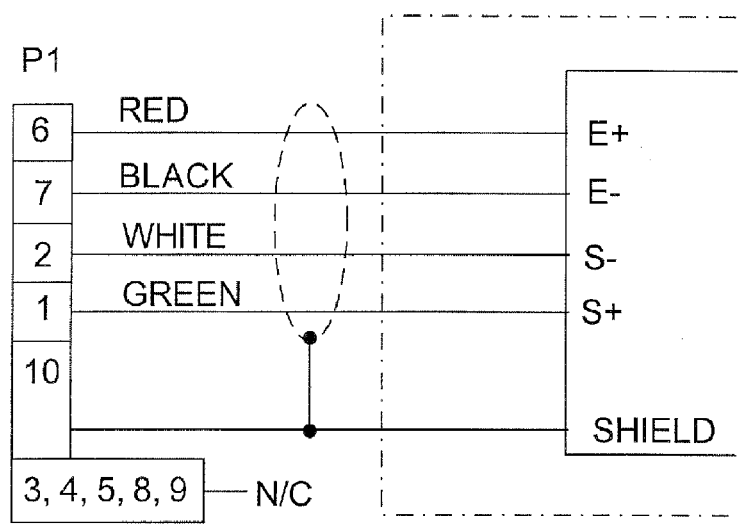
Figure 11A:
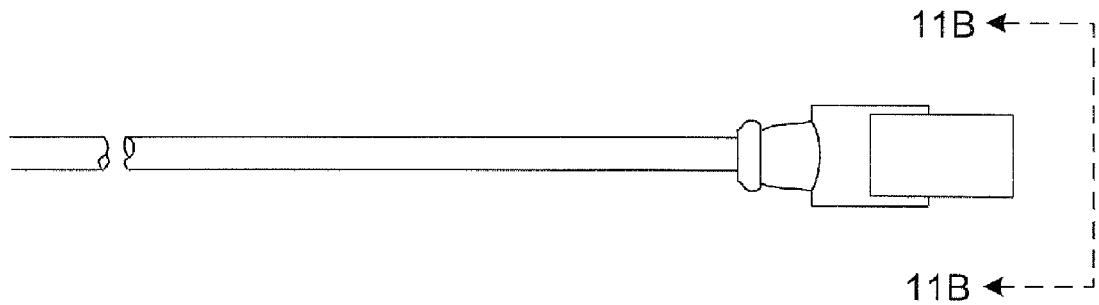
FIGS. 11A-11C illustrate yet another cable for interfacing a fetal scalp electrode with a maternal-fetal monitor, including the cable pinout diagram and the corresponding connector pinout for the fetal scalp electrode cable in a maternal-fetal monitor.
Figure 11B:
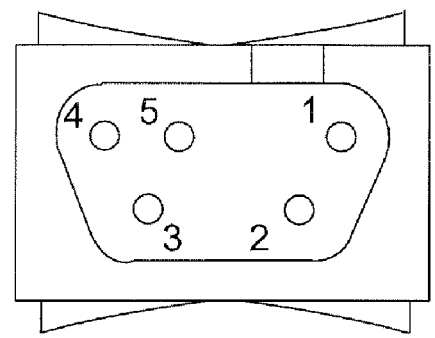
Figure 11C:
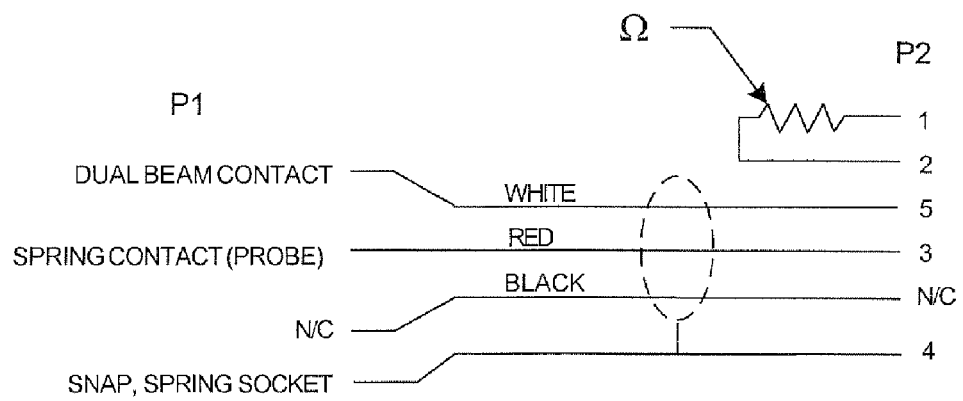
Figure 12A:
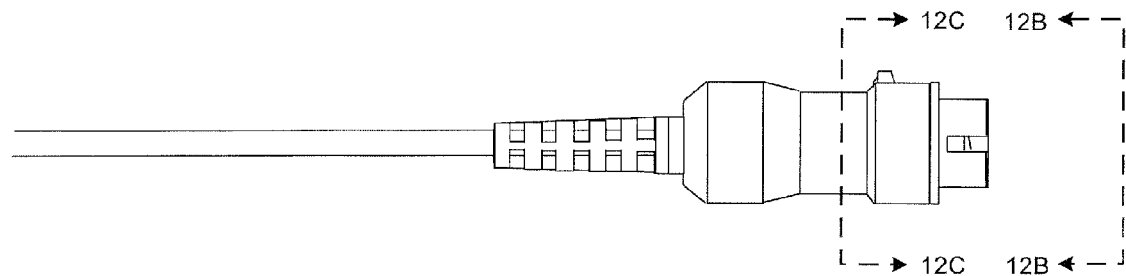
FIGS. 12A-12D illustrate another cable for interfacing an intra-uterine pressure catheter (IUPC) with a maternal-fetal monitor, including the cable pinout diagram and the corresponding connector pinout for the IUPC cable in a maternal-fetal monitor.
Figure 12B:
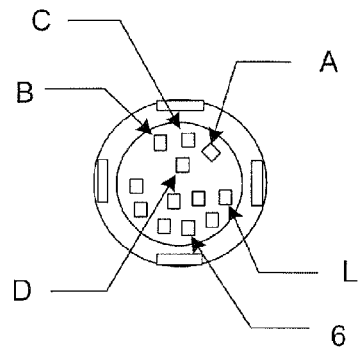
Figure 12C:
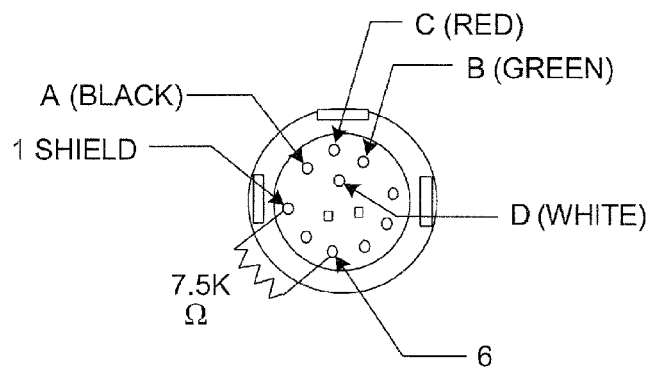
Figure 12D:
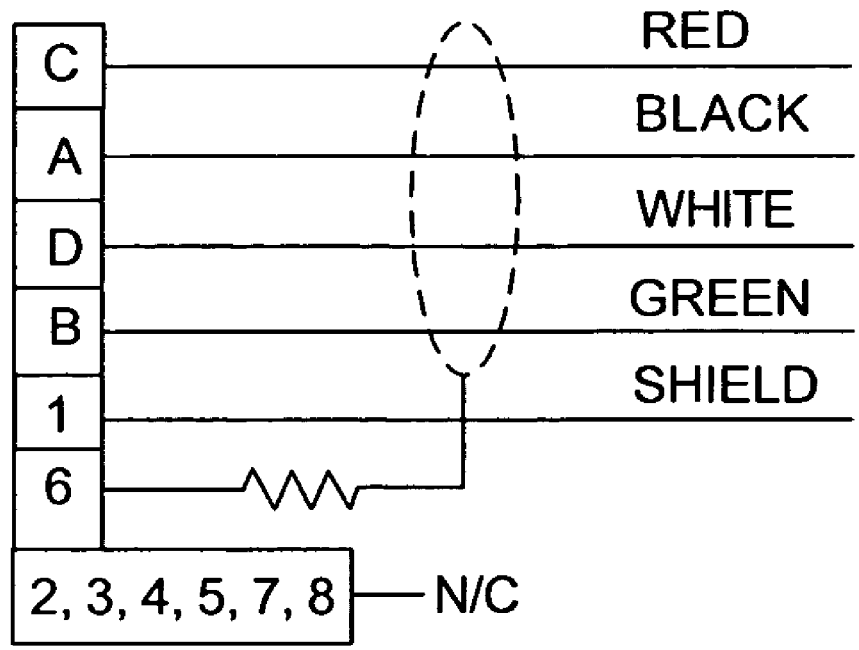
Figure 13:
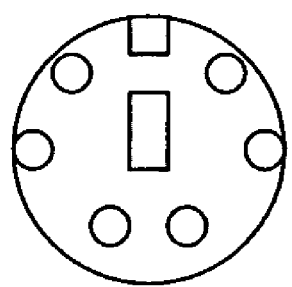
FIG. 13 illustrates a tocodynamometer connector pinout in a maternal-fetal monitor.

In the preferred embodiment, the signal converter of the invention includes a microprocessor, digital signal processor, or other programmable device that converts electrode signal data into an electrical analog of a Wheatstone bridge configuration that is normally used in a tocodynamometer. An illustration of a Wheatstone bridge configuration used in a conventional tocodynamometer is illustrated in FIG. 6. A tocodynamometer generally transforms strain to the strain gauge/sensor into a proportional change of resistance. Given the linear Wheatstone bridge configuration, differential output voltages are produced that are linearly related to the strain applied to the gauge/sensor. These differential output voltages are produced at the (+) and (−) pressure ports at mV amplitude levels. In certain instances, these small differential output voltages are subsequently amplified in the fetal/maternal monitor using a differential-input instrumentation amplifier configuration.

Figure 4:
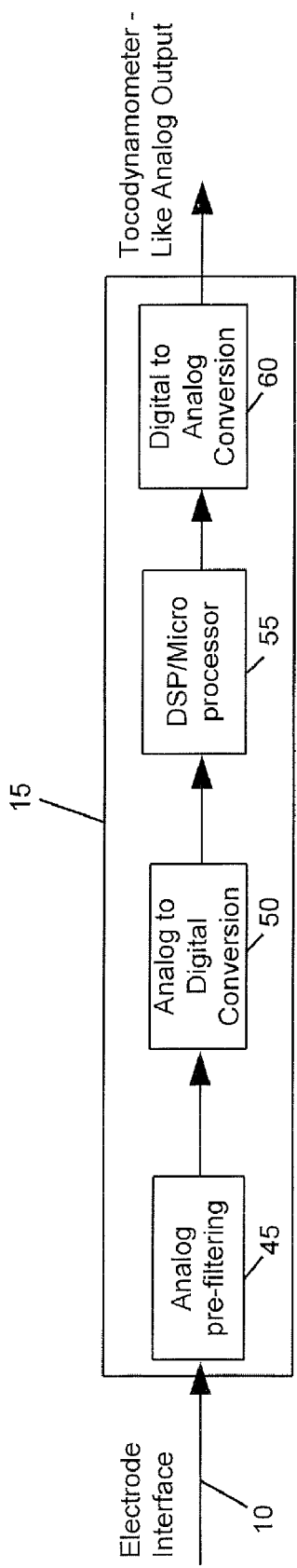
FIG. 4 is a flow diagram illustrating the process for converting electrode input to tocodynamometer-like data within the interface cable.

According to one embodiment of the subject invention, as illustrated in FIG. 4, the signal converter 15 includes a programmable device 55 and an analog to digital converter 50 that converts EHG signals derived from the electrode interface from analog signals to a digital output, where the digital output is then processed by the programmable device. The programmable device determines the appropriate voltage level required to mimic the output of the tocodynamometer or IUPC based upon the EHG digital output signals received. This voltage level can then be converted back to an analog signal using a digital to analog converter 60, pulse width modulation circuit, or other method.

In another embodiment, the signal converter includes a microprocessor 55 that calculates the desired uterine activity from the EHG signals. The microprocessor interfaces to the monitor via a microprocessor-controlled digital potentiometer, where the potentiometer simulates the strain gauge resistances seen at the legs of the Wheatstone bridge. This solution would mimic the tocodynamometer itself, instead of just the voltages output from the tocodynamometer. The desired signal would be driven on the Wheatstone bridge in a manner similar to the tocodynamometer itself, thus creating an EHG emulation of a tocodynamometer that is more compatible with different types of fetal monitors.

In certain embodiments, the microprocessor includes a means for filtering 45 of the signals generated from the electrodes. In one embodiment, the microprocessor includes: (1) a high pass filter at very low frequency (0.005 Hz) to remove the DC offset and noise, and (2) a low pass filtered with another low frequency filter (0.025 Hz). In a related embodiment, the microprocessor includes a high pass filter at a very low frequency and a standard power estimation method such as RMS or other squaring methods. More complex signal processing methods such as wavelets, blind source separation, nonlinear filtering, and frequency analysis can also be utilized.

Multiple signal channels can be included at the electrode interface to reduce noise characteristics. The multiple channels can be processed by the signal converter in many ways. For example, the signals can simply be added to each other or subtracted from each other for more robustness to noise. Additionally, attributes can be calculated on each signal and those signals with the best characteristics (e.g. signal to noise ratio) can be used to create the uterine activity signal.

In an alternative embodiment, the microprocessor and digital portion of the system would be replaced with a completely analog system. Analog filters can be created with resistors, capacitors, resistors and capacitors, and amplifiers can be embedded into the signal converter to convert the EHG signals to tocodynamometer-like signals. Analog circuitry can be designed using discrete components or integrated components such as ASICs (application specific integrated circuits). Since the conversion from EHG electrical interface to tocodynamometer or IUPC electrical interface is externally, simply a voltage conversion, analog filtering can be created to modify the EHG signals and create signals that mimic those expected by the fetal monitor.

In yet another embodiment, the signal converter includes both analog and digital processing. The analog processing would typically include pre- or post-processing of the signals. For example anti-aliasing filters or other filtering techniques can be implemented by the signal converter. Similarly, the signal converter could apply signal conditioning to the output signal to appropriately mimic the signal output from a tocodynamometer or IUPC.

Figure 5:
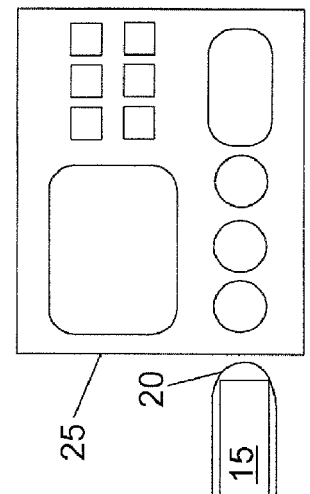
FIG. 5 illustrates another embodiment of the invention comprising a wireless interface connection between an electrode strip and maternal-fetal monitor.
Figure 5:
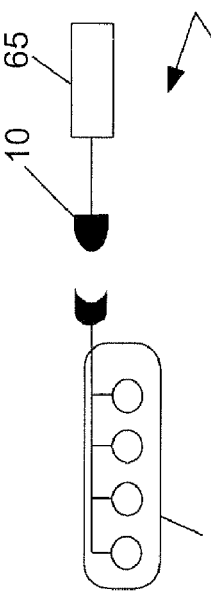

A wireless embodiment is contemplated herein, see FIG. 5. The interface system comprises an electrode interface 10, a wireless signal transmitter 65, a wireless signal receiver 70, a signal converter 15, and a maternal-fetal monitor port interface 20. According to the subject invention, these components can be physically independent from each other or presented in various combinations to form a single component. For example, the electrode interface and wireless signal transmitter can be presented together as a single component; the wireless signal receiver and signal converter can be presented together as a single component; the signal converter and wireless signal transmitter can be presented together as a single component; the maternal-fetal port interface, the signal converter, and the wireless signal receiver can be presented together as a single component.

According to one embodiment, a wireless signal transmitter is operably connected to an electrode interface, which is connected to the electrode(s). The wireless signal transmitter can include a data storage device (such as a magnetic hard drive, flash memory card, and the like). Preferably, the wireless signal transmitter includes communications protocols for data representation, signaling, authentication, and error detection that are required to send information over a wireless communications channel (i.e., a specific radio frequency or band of frequencies such as Wi-Fi, which consists of unlicensed channels 1-13 from 2412 MHz to 2484 MHz in 5 MHz steps). The wireless signal transmitter is preferably located in close proximity to the patient or on the patient's body. For example, the wireless signal transmitter can be attached to the side of the bed or the patient's arm. In certain embodiments, the signal converter is operably connected to the wireless signal transmitter or presented together with the wireless signal transmitter as a single component.

A wireless signal receiver is also included in the wireless embodiment. The wireless signal receiver is operably connected to a signal converter and/or maternal-fetal monitor port interface. The wireless signal receiver is preferably configured with communications protocols to receive information over a wireless communications channel.

Many wireless transmission communications protocols exist and are applicable to the wireless signal transmitter/receiver of this invention, including Bluetooth, Wi-Fi, Zigbie, wireless USB, etc. The wireless transmission of information from the wireless signal transmitter to the wireless signal receiver could be in digital format or in analog format.

In certain embodiments, the wireless signal transmitter (and/or wireless signal receiver) includes an internal power source (i.e., batteries, and the like). Alternatively, the wireless signal transmitter (and/or wireless signal receiver) does not require an internal power source. This is accomplished by using an antenna to convert radiated or inducted power into usable energy for the transmission of the desired signals. For example, the wireless signal transmitter can be an antenna that is commonly used in radio frequency identification tags (or RFID tags), where minute electrical current induced in the antenna by an incoming radio frequency signal provides just enough power for an integrated circuit (IC) in the RFID tag to power up and transmit a response (for example, to a wireless signal receiver of the invention).

In another embodiment, the EHG signal is digitized and stored in memory either in the electrode interface, the signal converter, or the maternal-fetal monitor port interface. The stored data can be transmitted periodically or at a later time. This delayed transmission may, without restriction, be utilized to improve battery life by transmitting data transiently, instead of continuously; or to allow for patient monitoring during disconnection from the monitor.

In operation, the electrode interface accepts EHG signals from the electrode(s) and transmits the signals to the maternal-fetal port interface via the wireless signal transmitter and wireless signal receiver. The signal converter can be operably connected to either the wireless signal transmitter or the wireless signal receiver, where the signal converter processes the electrode signals and/or performs digital/analog signal conversions.

In one embodiment, the electrode interface attached to the electrodes contains a signal converter that can perform analog to digital conversion and process EHG signals into an equivalent tocodynamometer or IUPC voltage. The wireless signal transmitter would then digitally transmit this data to the wireless signal receiver, which would communicate the data through the maternal-fetal port interface to the maternal-fetal monitor. Preferably, the data provided to the maternal-fetal monitor mimics data format normally provided by a tocodynamometer or IUPC.

In another embodiment, the electrode interface includes a means for converting analog signals to digital signals, and the resultant digital signals are transmitted via the wireless signal transmitter to the wireless signal receiver. The wireless signal receiver is operably connected to a signal converter that processes the digital signals into a format equivalent to tocodynamometer or IUPC data, which is subsequently communicated to the maternal-fetal monitor via the maternal-fetal monitor port interface.

In yet another embodiment, the raw analog signals generated by the electrodes are communicated via the electrode interface and wireless signal transmitter to a wireless signal receiver. The wireless signal receiver is operably connected to a signal converter that converts the raw analog signals to digital signals, which are subsequently processed by the signal converter into a format equivalent to tocodynamometer or IUPC data. The tocodynamometer or IUPC data is subsequently communicated to the maternal-fetal monitor via the maternal-fetal monitor port interface.

According to the present invention, the electrode interface can also be operably connected to a fetal heart rate sensor (such as an ultrasound or fetal scalp electrode). Data collected from the fetal heart rate sensor can be communicated to a maternal-fetal monitor via the cable embodiment or the wireless embodiment described above.

Figure 15:
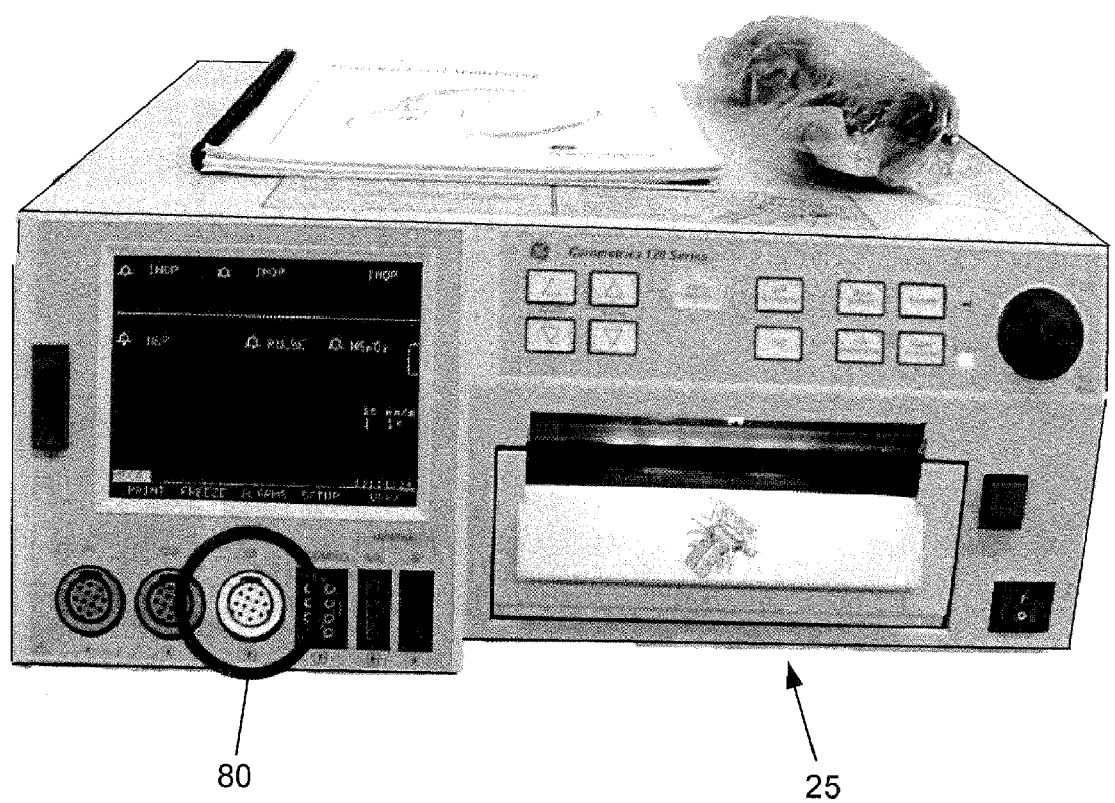
FIG. 15 illustrates a maternal-fetal monitor including a connector pinout suitable for use with the interface cable of the invention.

As illustrated in FIG. 15, the maternal-fetal monitor port interface of the invention can be operatively connected to a maternal-fetal monitor port 80 (also referred to herein as a pinout) configured for a conventional uterine activity sensor (such as a tocodynamometer, an intrauterine pressure catheter, a fetal scalp electrode, and the like). Preferably, the maternal-fetal monitor port interface is operably connectable with a uterine activity port or a tocodynamometer port available on a conventional maternal-fetal monitor 85.

The maternal-fetal monitor port interface preferably consists of appropriate connectors to maternal-fetal monitors from different manufacturers having different pinout/port configurations (see FIGS. 7-13). One such example of interfacing to both COROMETRICS® and AGILENT® is provided by the METRON® PS-320 patient simulator. This simulator uses a number of custom cables for interface to these monitors. Pinout/port information for commonly available maternal-fetal monitors are provided in Table 1.

TABLE 1

Uterine Activity Connector Pinout for Corometrics 116 Monitor

| Pin # | Signal Name | Signal Description |
|---|---|---|
| 1 | (+) Pressure | Positive Input to Pressure Amp |
| 2 | (−) Pressure | Negative Input to Pressure Amp |
| 3 | NC | No Connection |
| 4 | +4 Volt Excitation | +4 Volt Reference to Bridge |
| 5 | NC | No Connection |
| 6 | GND (Excitation Ref) | +4 Volt Reference Ground |
| 7 | UA Shield | Shield |
| 8 | NC | No Connection |
| 9 | NC | No Connection |
| 10 | NC | No Connection |
| 11 | IUP Enable | IUP ENABLE (ACTIVE LOW) |
| 12 | TOCO Enable | TOCO ENABLE (ACTIVE LOW) |

Example 1

As noted above, labor contractions are typically monitored with a strain gauge (such as a tocodynamometer), which provides frequency and approximate duration of labor contractions. Unfortunately, in obese patients, the distance from the skin to the uterus may be such that the tocodynamometer does not detect contractions reliably. In this setting, or when quantitative measurement of intrauterine pressure (IUP) is deemed necessary, an invasive IUP catheter is commonly required. The electrical activity of the uterus, or electrohysterogram (EHG) as monitored using electrodes, has long been recognized as linked to mechanical activity. This Example provides a study that compared the accuracy of EHG-derived contractions with those provided by a tocodynamometer and IUP monitoring in clinically severely obese laboring women.

Participants

This Example evaluated data from 14 laboring subjects with body mass index (BMI)≧34 who had an IUPC placed during EHG monitoring. Thirty minute segments were selected before and after placement.

Methods

An array of eight 3-cm$^2$ Ag/AgCl electrodes was placed over the maternal abdomen and signals amplified with high gain, low noise amplifiers. All signals were measured with respect to a reference electrode, with driven right leg circuitry to reduce common mode noise. The amplifier 3 dB bandwidth was 0.1 Hz to 100 Hz, with a 60 Hz notch. The contraction location was derived by down-sampling the signal at 20 Hz. Contractions were rejected if duration was less than 30 seconds or greater than 120 seconds, with an amplitude less than 30% of the median of the last 10 contractions (a minimum amplitude of 5 units was also applied for each tocodynamometer/IUPC, where the unit is mm HG for IUPC and the equivalent unit less height for tocodynamometer,). The contraction correlation index (CCI)=# consistent contractions/½(# tocodynamometer/IUPC-derived contractions+# MG-derived contractions) was evaluated. In addition, the frequency of unreliable uterine activity monitoring, using IUP as the standard for comparison, was also evaluated.

Results

Figure 14:
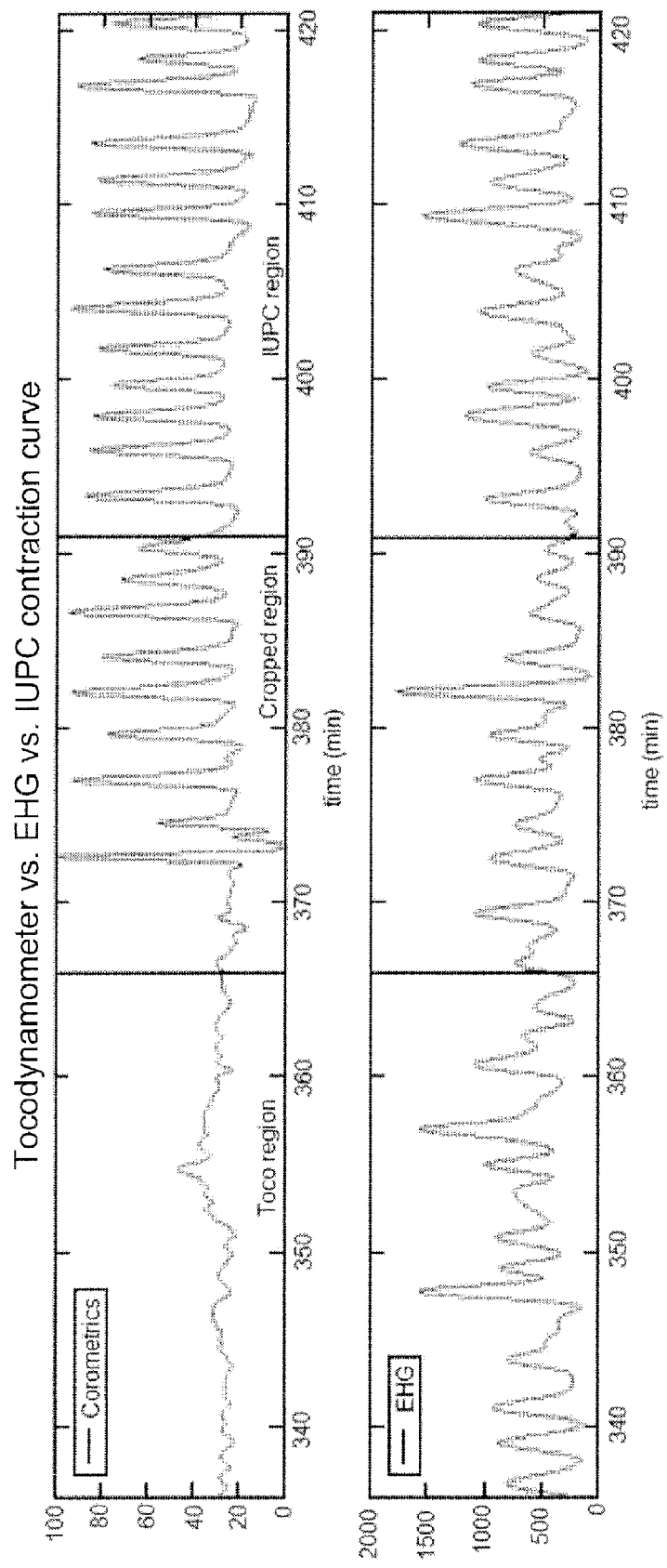
FIG. 14 illustrates the differences in accuracy for contraction patterns monitored in obese women with a tocodynamometer versus EHG-derived contraction patterns.

Of the 14 patients (BMI 45.1±7.9), 6 underwent amniotomy at the time of IUPC placement. During the first half of the study, the tocodynamometer identified 155 contractions while the EHG identified 195 contractions. After placement of the IUP, the IUP identified 192 contractions, versus 185 EHG-derived contractions. The CCI between EHG and the tocodynamometer was 0.79±0.29 and the CCI was 0.92±0.12 between EHG and IUP (p=0.07, ns). These results demonstrate that the tocodynamometer may be unreliable in clinically severely obese patients. As illustrated in FIG. 14, the EHG-derived contraction pattern in the obese women in this study correlated better with IUP than the tocodynamometer, exceeding 90% correlation in 13 out of 14 patients versus 10 out of 14 patients for the tocodynamometer.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for monitoring progress of labor, comprising:
   attaching at least one electrode onto a pregnant maternal abdomen;
   attaching to the electrode(s) an interface cable comprising,
      a first component that is an electrode interface that connects to the electrode(s) and that receives at least one electrode signal from the electrode(s),
      a second component that is a signal converter that connects to the electrode interface, wherein said signal converter receives the electrode signal(s) from the electrode interface and processes same said electrode signal(s) into electrical output data that mimics electrical output from a tocodynamometer or intra-uterine pressure catheter, and
      a third component that is a maternal-fetal monitor port interface that connects to a maternal-fetal monitor, wherein the maternal-fetal monitor port interface connects to the signal converter and receives and subsequently transmits the electrical output data to the maternal-fetal monitor; wherein the components are integrated to form a unitary structure in the cable; and
   assessing progress of labor by analyzing the electrical output data using the maternal-fetal monitor.

2. The method of claim 1, wherein the analysis of electrical output data generates any one or combination of data selected from the group consisting of: EHG data; uterine contractions during and after labor; uterine atony; intrauterine pressure; and Montevideo units.

3. The method of claim 1, wherein the pregnant maternal abdomen is of an obese patient.

4. The method of claim 1, wherein the signal converter processes same said electrode signals with an electrical analog of Wheatstone bridge configuration into electrical output data that mimics electrical output from said tocodynamometer.

5. An interface cable comprising:
   a first component that is an electrode interface for operably connecting to at least one electrode and receiving at least one electrode signal from the at least one electrode,
   a second component that is a signal converter that is connected to the electrode interface, wherein said signal converter receives the at least one electrode signal from the electrode interface and processes same said electrode signal(s) into electrical output data that mimics electrical output from a tocodynamometer or intra-uterine pressure catheter, and
   a third component that is a maternal-fetal monitor port interface for operably and physically connecting to a maternal-fetal monitor, wherein the maternal-fetal monitor port interface connects to the signal converter and receives and subsequently transmits the electrical output data to the maternal-fetal monitor,
   wherein the components are integrated to form a unitary structure in the cable.

6. The interface cable of claim 5, further comprising a means for filtering the at least one signal from the at least one electrode.

7. The interface cable of claim 6, wherein the filtering means is any one or combination of items selected from the group consisting of: high pass filters, low pass filters, multiple signal channels, analog filters, and digital filters.

8. The interface cable of claim 5, wherein the electrical output data is analog electrical output data.

9. The interface cable of claim 5, wherein the signal converter further possesses the ability to convert the electrode signal(s) into digital signal(s) and the digital signal(s) are converted into electrical output data that mimics electrical output from a tocodynamometer or intra-uterine pressure catheter.

10. The interface cable of claim 5, wherein the at least one electrode signal is communicated to the signal converter in analog format and the signal converter further possesses the ability to process and convert the electrode signal(s) in analog format into electrical output data that mimics electrical output from a tocodynamometer or intra-uterine pressure catheter.

11. The interface cable of claim 5, further comprising a power adapter.

12. The interface cable of claim 5, further comprising a digital-analog converter.

13. The interface cable of claim 5, wherein the maternal-fetal monitor port interface is comparable to a port interface selected from the group consisting of: an intrauterine pressure catheter-maternal-fetal port interface; a fetal scalp electrode-maternal-fetal port interface; and a tocodynamometer-maternal-fetal port interface.

14. The interface cable of claim 5, wherein the electrode(s) is selected from the group consisting of: printed circuit electrodes, disposable electrodes, reusable disc electrodes, headbands, and saline-based electrodes.

15. The interface cable of claim 14, wherein the electrode(s) is a type used for monitoring electrical activity selected from the group consisting of: electrocardiography (ECG/EKG); electroencephalography (EEG); electromyography (EMG); electronystagmography (ENG); electro-oculography (EOG), and electroretinography (ERG).

16. The interface cable of claim 5, wherein the signal converter processes same said electrode signals with an electrical analog of Wheatstone bridge configuration into electrical output data that mimics electrical output from said tocodynamometer.

* * * * *

UNITED STATES PATENT AND TRADEMARK OFFICE
CERTIFICATE OF CORRECTION

PATENT NO. : 7,828,753 B2
APPLICATION NO. : 11/582714
DATED : November 9, 2010
INVENTOR(S) : Neil Russell Euliano et al.

Page 1 of 1

It is certified that error appears in the above-identified patent and that said Letters Patent is hereby corrected as shown below:

Column 1,
Line 67, "Montevideo units" should read --montevideo units--

Column 9,
Line 16, "MG-derived" should read --EHG-derived--

Signed and Sealed this
First Day of February, 2011

David J. Kappos
*Director of the United States Patent and Trademark Office*